United States Patent [19]

Dahanayake et al.

[11] Patent Number: 5,686,024
[45] Date of Patent: Nov. 11, 1997

[54] AQUEOUS DISPERSION OF A SURFACE ACTIVE POLYMER HAVING ENHANCED PERFORMANCE PROPERTIES

[75] Inventors: Manilal S. Dahanayake, Princeton Junction; Tao Gao, Monmouth Junction; Eric H. Larson, Freehold, all of N.J.

[73] Assignee: Rhone-Poulenc Surfactants & Specialties, L.P., Cranbury, N.J.

[21] Appl. No.: 573,794

[22] Filed: Dec. 18, 1995

[51] Int. Cl.$^6$ .......................... B01F 17/18; B01F 17/28; C08F 16/28; C08F 20/56
[52] U.S. Cl. .................. 252/356; 252/3; 252/307; 252/311; 252/355; 252/357; 510/476; 524/457; 524/815; 526/146; 526/320
[58] Field of Search ...................... 252/3, 307, 311, 252/355, 356, 357; 510/476; 524/457, 815; 526/146, 916, 320

[56] References Cited

U.S. PATENT DOCUMENTS

| | | | |
|---|---|---|---|
| 3,480,546 | 11/1969 | Bashaw et al. | 252/3 |
| 3,718,609 | 2/1973 | Weimer | 252/307 X |
| 4,075,131 | 2/1978 | Sterling | 510/476 X |
| 4,215,028 | 7/1980 | Mizuguchi et al. | 526/146 X |
| 4,380,600 | 4/1983 | Hosoda et al. | 524/457 X |
| 4,454,060 | 6/1984 | Lai et al. | 510/429 |
| 4,678,606 | 7/1987 | Akhter et al. | 510/476 X |
| 4,713,182 | 12/1987 | Hiltz et al. | 252/307 X |
| 4,745,154 | 5/1988 | Ruffner | 524/801 |
| 4,772,462 | 9/1988 | Boothe et al. | 510/476 X |
| 4,871,594 | 10/1989 | Bister et al. | 524/815 X |
| 5,308,532 | 5/1994 | Adler et al. | 510/476 X |

FOREIGN PATENT DOCUMENTS

| | | | |
|---|---|---|---|
| 0231997 | 8/1987 | European Pat. Off. | A61K 7/08 |
| 0247766 | 12/1987 | European Pat. Off. | A61K 7/08 |

OTHER PUBLICATIONS

Search Report in PCT Counterpart Application of U.S. 08/573,794.

*Primary Examiner*—Richard D. Lovering
*Attorney, Agent, or Firm*—Paul J. Juettner; John Daniel Wood

[57] ABSTRACT

The present invention is directed to a new aqueous dispersion of surface active polymer which demonstrates enhanced surface active and performance properties more particularly as a foaming agent. The polymer comprises a vinyl monomer having at least one quaternized nitrogen atom, a vinyl monomer having at least one amide group, a vinyl monomer bearing both a hydrophobic and a hydrophylic group and optionally, a vinyl carboxylic monomer.

24 Claims, No Drawings

AQUEOUS DISPERSION OF A SURFACE ACTIVE POLYMER HAVING ENHANCED PERFORMANCE PROPERTIES

BACKGROUND OF THE INVENTION

1. Field of the Present Invention

The present invention relates to a new aqueous dispersion surface active polymer which demonstrates enhanced surface active and performance properties, a process of preparation thereof and its use in surfactant compositions as foaming agent.

2. Description of Prior Art

The foaming power of surfactants or their mixtures is an important property that has significant utility in various areas of use more particularly as personal care products, industrial and institutional products, agricultural, fire fighting and land fill applications. There has been considerable development effort to improve or enhance the foaming power of surfactants or their mixtures for these applications. It is known that it is difficult to improve foam height of an aqueous solution of surfactant or surfactant blend by more than about 5 millimeters by adding another chemical. Usually, solutions of different surfactant mixtures are not synergistic in foaming in that it is difficult for a blend of surfactants to exceed the individual performances provided by each surfactant.

Foam enhancement can be measured in three ways, i.e., foam height quantified by determining the foam height in millimeters after the surfactant solution is dropped into a receiver from a specified height (Ross-Miles foam test); foam density quantified by determining the weight of the foam cells per given volume; and foam stability also quantified by the Ross-Miles foam test which is expressed in either time (in seconds) required for foam to collapse to ½ of its original volume or in foam height (in millimeters) after a given time. The present invention is particularly directed to enhancing foam height.

It is known that in general foaming increases as the concentration of the surfactant increases until a concentration (which is usually greater than the Critical Micelle Concentration or CMC, i.e., the concentration at which micelle formation starts to take place) is attained after which foaming remains essentially constant providing that the solution viscosity has not been elevated to a point where foam height is decreased. In general, high viscosity of the solution will negatively affect foaming.

It is well known that the addition of polygalactomannans, e.g. guar gum, to surfactants will improve foam stability. The amounts of guar gum generally taught as needed to increase foam stability are not known to significantly affect or increase the foam height.

Recognizing the limitations on foaming caused by elevated viscosity, increases in foamability can be accomplished by increasing the content of surfactant. However, the greater the amount of surfactant or the greater the stability of the foam, the greater the tenancy for the waste water to foam requiring an increase use of defoamers in waste water treatment, either by industry or municipality water treatment systems. An environmentally sensitive foamable product would have the ability to provide desirable foam height with foam stability sufficient for the intended use but using less surfactant such that extensive defoaming prior to waste water treatment is less necessary.

Shampoo formulations containing guar gum(s) among other ingredients are disclosed in EPO Patents 0,231,997 and 0,247,766.

It has now been surprisingly found that surfactants in combination with a surface active polymer according to present invention using controlled amounts less than that normally used for foam stability will provide increased foaming.

SUMMARY OF THE INVENTION

Surface Active Polymer

In accordance with the present invention a new surface active polymer in aqueous dispersion form has now been found comprising:

(A) from about 0.1–95, more preferably from about 5–95, most preferably from about 20–95 weight percent based on total weight monomers of at least one vinyl monomer having at least one quarternized nitrogen atom;

(B) from about 0.1–95, more preferably from about 0.1–70, most preferably from about 0.1–60 weight percent based on the total weight of the monomers, of at least one vinyl monomer having at least one amidegroup;

(C) from about 0.5–75, more preferably from about 5–75, most preferably from about 10–75 weight percent based on the total weight of the monomers, of at least one vinyl monomer bearing both an hydrophobic and an hydrophylic group, and (D) from about 0–10, more preferably from about 0–5 weight percent, based on the total weight of the monomers, of at least one vinyl monomer bearing at least one carboxylic group, with the proviso that the sum of the percentages of monomers (A) to (D) is 100.

The ammonium monomers (A) are preferably of the formula:

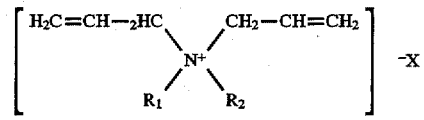

in which $R_1$ and $R_2$, identical or different are $C_1$–$C_6$ alkyl such as methyl, ethyl, propyl and hexyl. More preferably $R_1$ is the same as $R_2$ and is methyl or ethyl. Generally speaking the counter ion $(X)^-$ of the ammonium atom is any mineral and/or organic anion, such as chloride or sulfate. These preferred monomers are dimethyldiallylammonium chloride or sulfate and diethyldiallylammonium chloride or sulfate.

Others preferred monomers (A) are selected from the group consisting of: (meth)acryloyloxyethyltrialkylammonium (chloride or methylsulfate), (meth)acryloyloxyhydroxypropyltrialkylammonium (chloride or methylsulfate), (meth)acrylamidopropyltrialkylammonium (chloride or methylsulfate). It is also possible to use a precursor of monomer (A). This precursor can be a vinyl monomer having a nitrogen atom which can be subsequently quarternized during or after the polymerization.

These precursors can be selected from the group comprising:

-vinyl pyridine or vinylamines such as (meth)acryloyloxyethyltrialkylamine, (meth)acryloyloxyhydroxypropyltrialkylamine modified with glycidyltrialkylammonium chloride, -vinylamides such as (meth)acrylamide including N-substituted analogs thereof modified through the Mannich reaction, either pre or post polymerization, which can be subsequently quarternized with methylchloride, benzylchloride or dimethylsulfate, -(meth)acrylic acid modified with glycidyltrialkylammonium chloride during pre or post polymerization, -vinyl formamide hydrolyzed during pre- or post-polymerization, and the inorganic salt or quarternized derivatives thereof.

Other monomers containing amino or quaternary amino groups are disclosed in U.S. Pat. No. 3,766,156 the disclosure of which is incorporated herein by reference.

Suitable monomers (B) are for example of the formula:

$$H_2C=C(R_3)-C(O)-N(R_4, R_5)$$

in which $R_3$ is H or $C_1-C_6$ alkyl, $R_4$, $R_5$ identical or different are H or $C_1-C_{12}$ hydrocarbon radical such as alkyl, aryl, alkylaryl or arylalkyl. Examples of alkyl groups are methyl, ethyl, propyl, ethyl-2 hexyl and dodecyl, examples of aryl groups are phenyl and naphtyl, examples of alkyl aryl groups are methylphenyl, ethylphenyl, examples of arylalkyl groups are phenyl methyl and phenylalkyl.

Examples of suitable monomer (B) are (meth)acrylamide or an alkyl or dialkyl N-substituted (meth)acrylamide and N-(dimethylaminoethyl) acrylamide. It is possible to use a part of the monomer (B), as precursor monomers for at least a part of the monomer (A) for example by quarternizing (B), before or after polymerization with a quarternizing agent such as methylchloride as indicated above.

The polymer of the invention also comprises from about 0.5–40 of monomer (C), more preferably, from about 1–40, most preferably from about 10–30 weight percent of at least one vinyl monomer bearing both an hydrophobic acid an hydrophylic group, based on the total weight of the monomers. More particularly monomers (C) can be of the formula:

$$H_2C=C(R_6)-C(O)-O-[CH_2CH(R_7)O]_m-(CH_2CH_2O)_n-R_8$$

wherein $R_6$ is H or $C_1-C_6$ alkyl group, preferably H or methyl; $R_7$ is $C_1-C_4$ alkyl, preferably methyl; n is an average number from about 6–100, preferably 10–40 and m is an average number from about 0–50, preferably 0–10, provided that n is superior or equal to m and sum of (n+m) is about 6–100; $R_8$ is a hydrophobic $C_8-C_{40}$ linear or branched alkyl, alkylaryl, or arylalkyl group, preferably a $C_{18}-C_{30}$ alkyl, more preferably a $C_{22}$ behenyl radical or a tristyrylphenyl group of the formula:

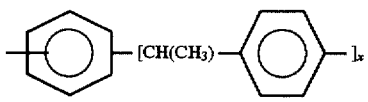

wherein x is an average number of from about 2 to about 3, wherein the substituent denoted x is randomly distributed around the benzene ring to which it is linked.

The above monomer can be obtained by the reaction of a vinyl monomer of an ester of (meth)acrylic acid with an alkoxylated alcohol or alkoxylated polystyryl phenol or by any other known process.

The vinyl monomer of the formula:

$$H_2C=C(R_6)-C(O)-O-[CH_2CH(R_7)O]_m-(CH_2CH_2O)_n-R_8$$

in which $R_6$, $R_7$, $R_8$, m and n have the meaning indicated above for the formula of monomer (C) are described in detail in European Patents EP 011.806, EP 013.836 and in U.S. patent application Ser. No. 08/317,261 filed Oct. 3, 1994, and now abandoned, the disclosures of which are incorporated herein by reference.

The polymer of the invention can also comprises for some purposes from 0 to about 10 weight percent of at least one vinyl monomer (D) bearing at least one carboxylic group, more particularily of the formula:

$$R_9CH=C(R_{10})COOH$$

in which $R_9$ is H, C(O)OY or $CH_3$, wherein when $R_9$ is H, $R_{10}$ is H, $C_1-C_4$ alkyl, or $CH_2COOY$; $R_9$ COOY, $R_{10}$ is H or $CH_2COOY$; or $R_9$ is $CH_3$, $R_{10}$ is H, Y is H or $C_1-C_4$ alkyl.

Among these monomers, acrylic or methacrylic acid or a mixture thereof with itaconic or fumaric acid are preferred, but crotonic and aconitic acid and half esters of these and other polycarboxylic acids such as maleic acid with $C_1-C_4$ alkanols are also suitable, particularly if used in minor amount in combination with acrylic or methacrylic acid. For most purposes, it is preferable to have at least about 0.5 weight percent and most preferably from about 1–5 weight percent of the carboxylic acid monomer.

The surface active polymer according to the present invention can be a statistical block or sequenced polymer. Most of the time it is a statistical polymer.

In a preferred embodiment of the present invention the relative quantity of monomers (A), (B), (C) and optionally (D) are chosen in order to provide a surface active polymer dispersion with a molecular weight $M_w$ between about 5,000 and about 5,000,000 more preferably between about 10,000 and about 2,000,000 dalton.

The term "vinyl monomer" as used herein means a monomer comprising at least one of the following groups:

$$CH_2=C, CH_2=CH, CH=CH$$

Polymerization of the Surface Active Polymer

The liquid dispersion copolymers of the invention can be conveniently prepared from the above-described monomers by conventional polymerization techniques in water at a pH lower than about 9.0 but greater than 3, preferably about 7 using free-radical producing initiators, usually in an amount from 0.01 percent to 3 percent based on the weight of the monomers. Polymerization at the above indicated pH permits direct preparation of an aqueous colloidal dispersion with relatively high solids content without problems of undue viscosity. The free-radical producing initiators conveniently are peroxygen compounds especially inorganic persulfate compounds such as ammonium persulfate, potassium persulfate, sodium persulfate; peroxides such as hydrogen peroxide; organic hydroperoxides, for example, cumene hydroperoxide, t-butyl hydroperoxide; organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite). These initiators are preferably water soluble such as:

2,2'azobis (N,N'-dimethyleneisobutyramidine) dihydrochloride 2,2'azobis (2-amidino-propane)dihydrochloride 2,2'azobis (N,N'-dimethyleneisobutyramidine)

Optionally a chain transfer agent can be used. Representative chain transfer agents include carbon tetrachloride, bromoform, bromotrichloromethane, long chain alkyl mercaptans and thioesters such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate. The chain transfer agents can be used in amounts up to about 10 parts per 100 parts of polymerizable monomers.

Optionally, other ingredients well known in the aqueous polymerization art may be included such as chelating agents, buffering agents, surfactants, inorganic salts and pH adjusting agents. The use of surfactants during the polymerization process is for example described in "Progress in Organic Coatings 24 (1994) 11–19", the disclosure of which is incorporated herein by reference.

Usually the copolymerization is carried out at a temperature between about 80° C. and 100° C. but higher or lower temperatures including polymerization under vacuum or pressure can be used. The polymerization can be carried out batchwise, stepwise or continuously with batch and/or continuous addition of the monomers in a conventional manner.

The monomers can be copolymerized in such proportions, and the resulting dispersion polymers can be physically blended, to give products with the desired balance of properties for specific applications. Minor quantities of a polyfunctional monomer, such as itaconic or fumaric acid to introduce a higher carboxylic acid content or limited crosslinking, provides further control of the structure of the polymer. Thus, by varying the monomers and their proportions, dispersion polymers having optimum properties for particular applications can be designed. Particularly effective liquid dispersion polymers can be obtained by copolymerization of about 0.1–95, more preferably 5–70 weight percent of monomer (A), about 0.1–95, more preferably 10–70, most preferably 20–60 weight percent of monomer (B), about 0.5–40, more preferably 3–35, most preferably 10–30 weight percent of monomer (C) and about 0–10, more preferably 0–5 weight percent of optional monomer(D), all percentages being based on the total weight of the monomers.

Foamable Surfactant Composition

The present invention also relates to a foamable surfactant composition with an increased foam height comprising:

a) a surfactant selected from the group consisting of a nonionic, anionic, cationic and zwitterionic surfactants and blends thereof in a total amount sufficient to produce a foam in water; and b) an aqueous dispersion of a surface active polymer as defined herein above including mixtures thereof, in an amount sufficient to increase foamability, i.e., foam height at least 5 millimeters, preferably at least 7.5 millimeters, more preferably at least 10 millimeters and more, over the foam height for the same level of surfactants without any surface active polymer, the foam height being measured by using the Ross-Miles Foam Test.

In a preferred embodiment, the foamable compositions of the invention comprise a surfactants selected from the group consisting of anionic, nonionic, and zwitterionic surfactant or mixtures thereof. The foamable composition can for example comprise a zwitterionic surfactant (when used as a sole surfactant), or blends of one or more further surfactants chosen from the other types such as cationic surfactants and mixtures thereof. It is understood that the surfactants are selected from chemically compatible surfactants as is the practice in the art.

Cationic surfactants are those surfactant compounds having a positive charge on the hydrophilic portion of the molecule. These compounds can be illustrated by alkyl imidazolines, e.g., oleyl imidazoline; ethoxylated amines, e.g., tallow ethoxylated amine, 5–15 EO; imidazoline quats, e.g. ditallow imidazolinium methyl sulfate; benzyl quats, e.g. benzyl trimonium chloride; and tetra alkyl quats, e.g., cetyl trimonium chloride. Some tetra alkyl quats when used as a sole surfactant have been found not to provide foam heights of at least 5 milliliters.

The anionic surface active compound is most preferably an alkyl sulfate, an alkyl ether sulfate (1–5 EO and/or PO) or mixtures thereof. These surfactants are generally employed in the form of their sodium, potassium, ammonium or mono-, di- or tri- ethanolamine salts. Examples of these surfactants are sodium lauryl sulfate, ammonium lauryl sulfate, mono-, di- and tri- ethanolammonium lauryl sulfates, sodium lauryl ether sulfate (e.g. 2EO), potassium lauryl ether sulfate (e.g. 3EO) and ammonium lauryl ether sulfate (e.g. 3EO).

Further suitable anionic surface active compounds include alkyl sulfosuccinates having the structure:

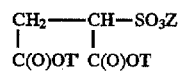

wherein T and T' represent the same or different straight chain or branched chain alkyl groups having from 5 to 14 carbon atoms and T can also equal Z; Z is a solubilizing cation chosen from alkali metal, more particulary sodium, ammonium, substituted ammonium and magnesium.

Particularly preferred dialkyl sulphosuccinates include those where T and T' represent $C_9$ and/or $C_{10}$ alkyl groups.

Still further suitable anionic Surface active compounds include α-olefin sulfonates, alkyl sarcosinates, alkyl monoglyceride sulfates, alkyl monoglyceride sulfonates, alkyl benzene sulfonates, monoalkyl ether sulfosuccinates, alkyl ether carboxylates, mono, and di-phosphate esters (alkyl, alkaryl and ethoxylate phosphate esters) including phosphate esters having higher ratios of mono to di, acyl isethionates and acyl methyl taurates.

Nonionic surfactants are those surfactants which have no electrical charge and can be illustrated by alkanolamides, alkyl phenol ethoxylates, fatty acid ethoxylates, alcohol ethoxylates, polyethylene glycol diesters, glycerol esters, galactoside uronates and alkylpoly glycosides. Examples of these nonionic surface active compounds include the reaction product of a sorbitan monolaurate or a sorbitan monococoate with from 20 to 80 moles of ethylene oxide and a $C_8$ to $C_{18}$ ethoxylated fatty alcohol having from 4 to 25 moles of ethylene oxide.

Examples of zwitterionic surfactant compounds, also including those compounds known as amphoterics, include amine oxides, e.g. lauramine oxide; betaines, e.g. alkyl amido betaines such as cocoamidopropyl betaine, alkyl dimethyl betaine, sulphobetaines, (sultaine, e.g. alkylether hydroxypropyl sultaine such as cocoamidopropyl hydroxysultaine) and imidazoline derivatives, e.g., sodium and disodium coco- or capryl- or tallo- or lauro- or stearroamphocarboxylates such as acetates, diacetates, propionates and dipropionates, and their acid counterparts, as well as their hydroxyalkyl sulfonates, iminocarboxylates such as acetates, diacetates, propionates and dipropionates, and alkyl glycine, e.g., dihydroxyethyl tallow glycinate.

The amount of surfactant compound present in the foamable compositions of the invention will depend on the product form of the final composition. For example, the product can be in a propellant-free liquid or gel intended to be poured, sprayed, pumped or otherwise dispensed on to the surface to be contacted. The product can also be in the form of a liquid or gel containing a gaseous liquafiable propellant, or dispensed from an aerosol type container.

Generally the surfactant is sufficient in quantity to provide effective foaming for the area of use. Some areas of use require high foaming such as in light duty consumer laundry detergents, carpet cleaners, personal care products including shampoos, bath preparations, liquid soaps, shaving soaps, toilet bars, hair care and grooming products, agricultural and pesticide application foams and fire fighting foams. In general, effective foams can be prepared using from about 20% to about 0.01%, and preferably from about 5% to about 0.1% by weight active surfactant in the final foamable composition.

The individual amounts of cationic, anionic, nonionic and zwitterionic surface active compound(s), when present alone or in admixture, will fall within limits for total surfactant compound as defined herein, i.e., from 20% to 0.01%, preferably from 5% to 0.1% by weight of the final composition.

The surface active agent is present in an amount sufficient to increase foam height and insufficient to cause a decrease in foam height over that obtainable using the surfactant(s) alone. Preferably, the surface active agent is present in an amount (dry extract) ranging from about 0.05% to about 2.0%, preferably from about 0.05% to about 15% and more preferably from about 0.08% to about 4% by weight based on the total weight of the surfactant(s) in the composition.

The foaming composition of the invention is an aqueous system and, at the time of foaming, generally contains from about 80% to about 99.95% water. Foamable concentrates can be formed using less water as desired. Foamable concentrates will have the same ratio of polymer to surfactant as expressed herein before.

The foamable compositions of the invention can contain various optional ingredients particularly adapted to provide other effects and which are conventionally employed in the manufacture of like foamable compositions, including but not limited to dyes, perfumes, salts, opacifiers, thickening agents such as water soluble polymers, hair and skin conditioning agents, stabilizers, preservation agents, and the like.

The foamable compositions of the present invention provide high foaming with less surfactant which foams are sufficiently stable for their initial purpose and then are easily broken for ease of disposal, whether in a consumer or industrial environment. The use of less surfactant to achieve an acceptable level of foam in addition to easy foam breaking provides environmentally sound compositions that are easier to dispose of in waste water treatment. These properties make these compositions adaptable for use in products ranging from cosmetics to industrial applications and are usable wherever foamable compositions have found use. These products are particularly useful for shampoos, including baby shampoos, body shampoos including bubble baths, bar soaps, bath gels, hair conditioning gels, lotions, skin creams and lotions, make up removal creams and lotions, liquid detergents, dish detergents and other washing and cosmetic products, agricultural marking foams, seed treatment foams, pesticide application foams, land fill foams and fire fighting foams.

The present invention is now more fully illustrated in the examples which follow. The percentage of ingredients of the products prepared in the examples is based on total solution weight and the percentage given in the claims is on a weight basis. DMDAC is intended to mean dimethyldiallylammonium chloride and BEM is a behenyl ethoxymethacrylate of the formula:

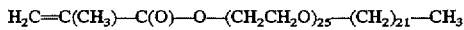

$H_2C=C(CH_3)-C(O)-O-(CH_2CH_2O)_{25}-(CH_2)_{21}-CH_3$

EXAMPLE 1

A) Polymerization of a surface active DMDAC/BEM/Acrylamide polymer.

A reactor comprising a 1 liter electrically heated resin flask with a four neck top was utilized. A condenser using tap water as the cooling medium was fitted to one neck; the agitator shaft entered through the central neck, sealed through a Teflon fitting and a O-ring lubricated with silicone grease; monomer was fed through a stainless steel tube inserted in a rubber stopper in the third neck; a temperature probe, initiator feed and $N_2$ were fed through tubing in a rubber stopper in the fourth neck. The condenser discharge was bubbled through water to maintain a positive pressure in the reactor.

Agitation was provided by a stainless steel 5.2 millimeter diameter Lightin' high efficiency axial flow turbine set near the bottom of the flask, operating at 500 RPM.

Temperature was controlled via a temperature sensor connected to a three mode controller using time-proportioning to modulate the electrical heating of the reactor.

Monomer was fed into the reactor using a positive displacement pump over a two hour period.

Initiator solution was fed into the reactor using a separate positive displacement pump over the same two hours period.

Nitrogen was sparged into the reactor mass at a rate sufficient to maintain a positive pressure of about 1 Hg centimeter. For most reactions this corresponded to a flow rate of about 0.75 liter/min at 3 bars.

Initially, the reactor charge (RC) had the following composition: 0.16 gm ammonium persulfate, 0.026 gm Versenex 80 (40% diethylentriamine pentaacetic acid or DTPA solution and 200 gm of deionized water were introduced into the reactor and thereafter the monomer feed and the initiator feed were introduced into the reactor.

The monomer feed (MF) had the following composition:

27.4 gm of) monomer (BEM) having the formula:

$H_2C=C(CH_3)-C(O)-O-(CH_2CH_2O)_{25}-(CH_2)_{21}-(CH_3)$ 110 mg of a 52.5% aqueous acrylamide solution, 23.9 gm of 62% aqueous solution of dimethyldiallylammonium chloride (DMDAC) and 95.2 gm of deionized water and 13.7 gm of MAA (methacrylic acid).

The initiator feed (I.F) had the following composition:

1.08 gm of ammonium persulfate, 60 ml of deionized water and one drop of 15% aqueous NaOH (by weight).

The reaction was performed at pH about 7 and at a temperature of 90° C. The reaction mass was held at 90° C. after completion of feed of initiator and monomer for 30 minutes.

The polymer obtained had an estimated molecular weight of 50,000 dalton.

EXAMPLE 2

In order to demonstrate the effectiveness of the invention various surfactants were combined with the aqueous dispersion of the surface active polymer (P) obtained in Example 1 and compared against control formulations of the surfactant(s) containing no surface active agent polymer. The surfactants studied and reported in these examples are outlined in Table 1 herein after.

TABLE I

| Surfactant Class | Surfactant Subclass | Surfactant Trade Name | Surfactant Chemical Name | Surfactant Short Handed Name |
|---|---|---|---|---|
| Zwitterionics | Amine Oxide | RHADAMOX LO | Lauramine Oxide | LO |
| | Amphoglycinate | MIRANOL C2M | Sodium Cocoamphodiacetate | C2M |
| | Amphoglycinate | MIRANOL Ultra C-32 | Sodium Cocoamphoacetate ultra purified | C32 |
| | Betaine | MIRATAINE CB | Cocoamidopropyl Betaine | CB |
| Anionic | Alkylsulfate | RHODAPON SB | Sodium Dodecyl Sulfate | SB |
| | Alkylether Sulfate | RHODAPEX ES | Sodium Laureth (3) Sulfate | ES |
| | Alkylether Sulfate | RHODAPEX ESY | Sodium Laureth (1) Sulfate | ESY |
| | Alkylsulfate | RHODAPON LSB | Sodium Lauryl Sulfate | LSB |
| Surfactant blend | Alkylsulfate + Alkylether Sulfate | AGRHO FM-3800 | Sodium Dodecyl Sulfate Sodium Laureth (1) | FM |
| Surfactant blend | Alkylsulfate + Betaine | MIRACARE BC-10 | Cocoamidopropyl Betaine + PEG (80) Sorbitan Laurate | BC-10 |
| Surfactant blend | Alkylsulfate + Betaine | MIRACARE BC-20 | Cocoamidopropyl Betaine + PEG (80) Sorbitan Laurate | BC-20 |
| Nonionics | Alkylanolamide | ALKAMIDE DC 212/S | Cocoamide DEA (1/1) | DC 212 |

Foamability of the product was evaluated using the Ross-Miles Foam Height Test as outlined in ASTM method D1173 and compared to a control system without added polymer (P) which is the surface active polymer of the present invention. The test comprises dropping a measured amount of surfactant solution from a specific height into a receiver of standard dimensions using a constant volume of solution of 250 milliliters at a constant temperature and recording the initial foam height above 250 milliliters (Initial Foam Height—FHi), and the foam height above 250 milliliters after five minutes (Foam Height at 5 minutes—FH5). The foam was evaluated and the following results were obtained and are gathered in Table 2 and Table 3 hereinafter:

TABLE 2

Foaming Height of Surfactant Systems in Absence or Presence of Surface Active Polymer(P)(pH = 10.0)

| | Ross-Miles foaming height (mm) Hi–Hf (after 5') | | |
|---|---|---|---|
| Surfactant System (1% w.t.) | Surfactant no(P) | plus (P) (0.02% w.t.) | plus (P) (0.1% w.t.) |
| Miranol Ultra C-32 | 182–161 | 195–171 | 205–180 |
| Miranol C-2M | 185–173 | 202–173 | |
| Miracare BC-10 (5% w.t.) | 215–180 | 216–184 | 231–193 |
| Rhodapon LSB | 191–172 | 208–186 | 215–195 |
| Rhodamox LO | 178–30 | 194–164 | 200–170 |
| Rhodapex ESY | 183–165 | 204–179 | 210–185 |
| Rhodapon SB | 199 | 210 | |
| Mirataine CB | 182–169 | 197–172 | 205–180 |
| Rhodapex ES | 189 | | |
| ES-LO | 200–175 | | 225–195 |
| ESY-LO | 209–180 | 218–191 | 240–201 |
| LSB-LO | 212–176 | 235–189 | 241–201 |
| SB-LO | 212–181 | | 244–205 |
| Ultra 32-SB | 195–175 | | 230–198 |
| Ultra 32-LO | 190–172 | | 205–182 |
| Ultra 32-ESY | 195–175 | | 235–197 |
| CB-ESY | 210–177 | 222–198 | 238–202 |

*The ratio of surfactants is 1:1 for all studied binary surfactant systems.

TABLE 3

Foaming Height of Surfactant Systems in Absence or Presence of Polyacrylamide Copolymers (pH = 6.0)

| | Ross-Miles foaming height (mm) Hi–Hf (after 5') | | |
|---|---|---|---|
| Surfactant System (1% w.t.) | FHi Fhf no(P) | plus (P) (0.05% w.t.) | plus (P) (0.1% sw.t.) FHi FHf |
| Miracare BC-10 (5% w.t.) pH = 8.0 | 187 162 pH = 8.0 | 207 175 pH = 8.0 | |
| Miracare BC-20 (5% w.t.) pH = 8.0 | 200–169 pH = 8.0 | 224–191 pH = 8.0 | |
| AgRHO FM-3800 | 198–171 | 221–187 | 232–195 |
| Rhodapon LSB | 180–172 | | 215–185 |
| Rhodamox LO | 192–165 | | 210–175 |
| Rhodapex ESY | 185–175 | 200–185 | 210–190 |
| Rhodapon SB | 199–178 | | 212–195 |
| Mirataine CB | 188–175 | | 205–185 |
| Miranol Ultra C-32 | 194–176 | | 210–180 |
| LSB-LO(1/1) | 209–180 | | precipitate |
| Ultra 32-SB (1/1) | 218–192 | | 242–205 |
| Ultra 32-ESY (1/1) | 209–183 | 238–204 | 241–209 |
| CB-ESY (1/1) | 208–204 | | 236–204 |
| ESY-DC212 (8/2) | 200–180 | 220–196 | |
| ESY-DC212/S-Mirataine CB (10/2/1.2) | 199–177 | 220–193 | |

*The ratio of surfactants is 1:1 for all studied binary surfactant systems.

As it appears from the tables 2 and 3, initial foam heights at pH=6 were found enhanced by about at least 9 millimeters with polymer (P) with an amount of (P) of 0.02%, and by at least 15 millimeters with a quantity of (P) of 0.1%. These foam heights are most of the time greater at pH=10.

What is claimed is:

1. An aqueous dispersion of a surface active polymer from polymerization of monomers comprising:

A) from about 0.1–95 weight percent based on total monomers of at least one monomer having the formula:

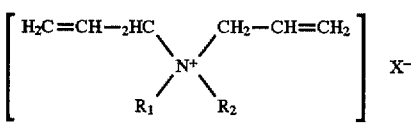

in which $R_1$ and $R_2$, identical or different are $C_1$–$C_6$ alkyl, and $X^-$ is mineral and/or organic anion, B) from about 0.1–95 weight percent based on total monomers of at least one vinyl monomer having at least one amide group, C) from about 0.5–75 weight percent based on total monomers of at least one vinyl monomer of the formula:

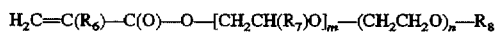

in which $R_6$ is H or $C_1$–$C_6$ alkyl group; $R_7$ is $C_1$–$C_4$ alkyl; n is an average number from about 6–100 and m is an average number from about 0–50 provided that n is superior or equal to m and the sum of (n+m) is about 6–100, $R_8$ is a hydrophobic $C_8$–$C_{40}$ linear or branched alkyl, alkylaryl, or arylalkyl group, and D) from 0 to about 10 weight percent based on total monomers of at least one vinyl carboxylic monomer of the formula:

in which $R_9$ is H and $R_{10}$ is H, $C_1$–$C_4$ alkyl, or $CH_2COOY$; $R_9$ is COOY, and $R_{10}$ is H or $CH_2COOY$; or $R_9$ is $CH_3$ and $R_{10}$ is H and Y is H or $C_1$–$C_4$ alkyl.

2. An aqueous dispersion of claim 1, wherein monomer (A) is dimethyldiallylammonium chloride or sulfate.

3. An aqueous dispersion of claim 1, wherein monomer (A) is diethyldiallylammonium chloride or sulfate.

4. An aqueous dispersion of claim 1, wherein monomer (A) is selected from the group consisting of:

(meth)acryloyloxyethyltrialkylammonium (chloride or methylsulfate), (meth)acryloyloxyhydroxypropyltrialkylammonium (chloride or methylsulfate), and (meth)acrylamidopropyltrialkylammonium (chloride or methylsulfate).

5. An aqueous dispersion of claim 1, wherein monomer (B) is in the form of a precursor selected from the group consisting of:

vinyl pyridine or vinylamines, vinylamides which can be subsequently quarternized with methylchloride, benzylchloride or dimethylsulfate, (meth)acrylic acid modified with glycidyltrialkylammonium chloride, hydrolyzed vinyl formamide, and the inorganic salt or quarternized derivatives thereof.

6. An aqueous dispersion of claim 1, wherein monomer (B) is of the formula:

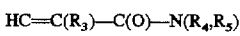

in which $R_3$ is H or $C_1$–$C_6$ alkyl, $R_4$, $R_5$ identical or different are H or $C_1$–$C_{12}$ hydrocarbon radical.

7. An aqueous dispersion of claim 1, wherein monomer (C) is of the formula:

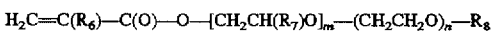

in which $R_6$ is H or methyl; $R_7$ is methyl; n is an average number from about 10–40 and m is an average number from about 0–10 provided that n is > or =m and sum of (n+m) is about 6–100; $R_8$ is an hydropholic $C_8$–$C_{40}$ linear or branched alkyl, alkylaryl or arylalkyl group.

8. An aqueous dispersion of claim 7, wherein $R_8$ is $C_{18}$–$C_{30}$ alkyl radical.

9. An aqueous dispersion of claim 7, wherein $R_8$ is a behenyl radical.

10. An aqueous dispersion of claim 7, wherein $R_8$ is of the formula:

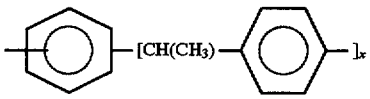

x is an average number of from about 2 to about 3, wherein the substituent denoted x is randomly distributed around the benzene ring to which it is linked.

11. An aqueous dispersion of claim 1, wherein monomer (D) is of the formula:

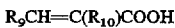

in which $R_9$ is H, C(O)OY or $CH_3$, wherein when $R_9$ is H, $R_{10}$ is H, $C_1$–$C_4$ alkyl, or $CH_2COOY$; $R_9$ is COOY, $R_{10}$ is H or $CH_2COOY$; or $R_9$ is $CH_3$, $R_{10}$ is H, Y is H or $C_1$–$C_4$ alkyl.

12. An aqueous dispersion of claim 1, wherein monomer (D) is acrylic or methacrylic acid or a mixture thereof with itaconic or fumaric acid.

13. An aqueous dispersion of claim 1, wherein the molecular weight Mw of said surface active polymer is comprised between 5,000 and 5,000,000 dalton.

14. A process for making the aqueous dispersion of surface active polymer of claim 1, comprising copolymerizing in water the monomeric mixture (A) through (D) as defined in claim 1 at a pH of lower than about 9.0, but greater than 3 in the presence of a free-radical producing initiator.

15. A process of claim 14, wherein the polymerization temperature is about 80° C. to 100° C.

16. A process of claim 14, wherein water soluble initiator is used.

17. A process of claim 14, wherein no emulsifier is used.

18. A process of claim 14, wherein a part of monomer B is quarternized with a quarternizing agent.

19. A foamable surfactant composition characterized by increased foam height comprising:

a) a zwitterionic surfactant as the sole surfactant in an amount sufficient to produce a foam in water; and b) an aqueous dispersion of surface active polymer as defined in claim 1 in an amount sufficient to elevate the initial foam height of an aqueous solution of said zwitterionic surfactant at least 5 millimeters above a control of the surfactant without said surface active polymer, using the Ross-Miles Foam Test.

20. A foamable surfactant, according to claim 19, further comprising at least another surfactant selected from the group consisting of anionic, nonionic and cationic surfactants.

21. A foamable surfactant composition characterized by increased foam height comprising:

a) an anionic surfactant as the sole surfactant in an amount sufficient to produce a foam in water; and b) an aqueous dispersion of surface active polymer as defined in claim 1 in an amount sufficient to elevate the initial foam height of an aqueous solution of said anionic surfactant at least 5 millimeters above a control of the surfactant without said surface active polymer, using the Ross-Miles Foam Test.

22. A foamable surfactant, according to claim 21, further comprising at least another surfactant selected from the group consisting of zwitterionic, nonionic and cationic surfactants.

23. A foamable surfactant composition characterized by increased foam height comprising:

a) an nonionic surfactant as the sole surfactant in an amount sufficient to produce a foam in water; and b) an aqueous dispersion of surface active polymer as defined in claim 1 in an amount sufficient to elevate the initial foam height of an aqueous solution of said nonionic surfactant at least 5 millimeters above a control of the surfactant without said surface active polymer, using the Ross-Miles Foam Test.

24. A foamable surfactant, according to claim 23, further comprising at least another surfactant selected from the group consisting of zwitterionic, anionic and cationic surfactants.

* * * * *